United States Patent [19]

London

[11] Patent Number: Plant 7,635

[45] Date of Patent: Aug. 27, 1991

[54] SPATHIPHYLLUM PLANT NAMED PRINCESS

[75] Inventor: Christopher J. London, Orlando, Fla.

[73] Assignee: New Gene Research & Development, Orlando, Fla.

[21] Appl. No.: 506,767

[22] Filed: Apr. 10, 1990

[51] Int. Cl.[5] ..... A01H 5/00
[52] U.S. Cl. ..... Plt./88
[58] Field of Search ..... Plt./88

[56] References Cited

U.S. PATENT DOCUMENTS

P.P. 5,863 1/1987 Caldwell ..... Plt. 88
P.P. 6,144 4/1988 Caldwell ..... Plt. 88
P.P. 6,145 4/1988 Caldwell ..... Plt. 88

*Primary Examiner*—Howard J. Locker
*Attorney, Agent, or Firm*—Foley & Lardner

[57] ABSTRACT

A Spathiphyllum plant named Princess characterized by its relatively short growth habit, narrow and oblong thick dark green leaves, and relatively small and rounded white spathes which are carried above the leaves on straight, wiry pedicels.

1 Drawing Sheet

The new cultivar is a Spathiphyllum hybrid known by the cultivar name Princess. Princess is the product of a breeding program carried out by the inventor Christopher London in Apopka, Fla. The male parent of Princess was the Spathiphyllum hybrid Mauna Loa. The Female parent was an unnamed cultivar of the species *Spathiphyluum wallisii.* The new cultivar was discovered and selected by Christopher London in Genera, Fla. Subsequent propagation by division increased the number of plants for evaluation and demonstrated the stability of the combination of characteristics of Princess from generation to generation.

The following observations, measurements and values describe plants grown in Palmdale, Fla. under greenhouse conditions which closely approximate those generally used in horticultural practice.

The following characteristics of Princess have been repeatedly observed and in combination distinguish Princess from other Spathiphyllum cultivars, particularly the cultivar Londonii with which it can be compared.

1. Princess is shorter in stature than Londonii.
2. The leaves of Princess are narrower and more oblong that the leaves of Londonii.
3. Princess has whiter flowers than Londonii.
4. Princess has smaller and more round flowers than Londonii.
5. Except for the differences in characteristics noted, Princess is generally similar to Londonii.

All color references are measured against the Royal Horticultural Society Colour Chart. Color values are as close as possible but approximate to the extent that color depends on horticultural practices such as light level, temperature and fertilization rate, among others.

The accompanying color photographic drawing comprises a front perspective view of Princess, with colors being as nearly true as possible with illustrations of this type.

Origin: Seedling.
Classification: Spathiphyllum hybrid cv. Princess.

Propagation: Asexual production either by tissue culture or division.

Plant: In a 6" pot, Princess will be at the mature size of approximately 25 cm. to 35 cm. in height and approximately 50 cm. to 60 cm. in width after approximately 50 weeks under normal and appropriate growing conditions, produced from a tissue culture liner.

Leaves:

*Form.*—The leaf blade is ovate, having an cuspidate-acuminate tip and a acute base. The margins are entire and very wavy along the edge. The midrib tends to curve down at the tip. The leaf blade is thick and tends to be straight at the base and curve up near the tip over the width of the leaf. The leaf surface is shiny with a ribbed appearance.

*Size.*—Leaves of a mature plant as defined above are approximately 18 cm. to 22 cm. in length and approximately 9 cm. to 11 cm. in width.

*Petiole.*—The petiole is approximately 15 cm. to 16 cm. in length from the base of the petiole to the base of the leaf blade on the primary shoot. Secondary shoots may be somewhat smaller depending on the age of the shoot. The petiole is approximately 4 mm. to 6 mm. in diameter just below the geniculum. The petiole curves at the geniculum.

*Petiole wings.*—Petiole wings are approximately 12 cm. to 13 cm. in length and approximately 1 cm. in width at the midpoint. The tip of the petiole wings are acuminate. There is approximately 2.5 cm. to 3.5 cm. between the top of the wing and the base of the leaf.

*Geniculum.*—The geniculum is curved and approximately 1.5 cm. to 2.5 cm. in length and approximately 1 cm. in diameter. The color is greener than 145B, and greyer than 143C. There is no space between the top of the geniculum and the base of the leaf blade. The geniculum is prominent.

*Veins.*—Veins are sunken, with the leaf blade rounded between veins on the upper surface. Veins are protruding on the under surface. There are approximately 10 to 14 primary veins on the leaf.

*Color.*—Mature leaf: Upper surface: Darker green than 137A, lighter than 139A. Under surface of midrib: Darker green than 137A, lighter than 139A. Under surface of midrib: Greener than 145 B, greyer than 143C. Petiole: Greener than 137A. Petiole wing: Greener than 137A.

INFLORESCENCE

Immature: The spathe is tightly rolled around the spadix and extrudes from the petiole sheath. The spathe is fully open approximately when the pedicel is fully elongated — approximately 46 cm. to 50 cm. above the soil surface.

Mature:

*Spathe.*—Size: The flattened spathe is approximately 12.5 cm. to 13.5 cm. high and approximately 8 cm. to 9 cm. in width. Color: Fully open: Front: 155A. Back: 155A. Faded: Front: 143C. Back: 143C.

*Arrangement.*—The spathe stands up on straight wiry pedicels and opens vertically above the leaves.

*Shape.*—The spathe is oval with an aristate apice that is straight. The base is acute-obtuse. The spathe is deeply cupped when first open, and is approximately 11 cm. to 13 cm. in height, approximately 6 cm. to 7 cm. in width, and approximately 15 mm. to 22 mm. in depth.

*Flowering time.*—After approximately 50 weeks, for an untreated plant depending on season, approximately 1 to 3 blossoms will be present. Smaller blossoms may occur on less mature growth.

REPRODUCTIVE ORGANS

Spadix:

*Size.*—Approximately 5 cm. to 6 cm. in height and approximately 13 mm. to 17 mm. in width.

*Color.*—When the spathe unrolls, the spadix is 9D.

*Stamens.*—Anthers and filaments are not clearly visible.

*Pollen.*—White in color.

*Pistil.*—9D in color, protruding between the staminate flowers, firmly fixed to the main axle. The pistilate flowers extend approximately 3 mm. beyond the staminate flowers.

Roots: White fleshy roots with fine laterals.

General observations:

Spathiphyllum hybrida Princess is a shorter plant than the cultivar Londonii and has smaller, more round flowers. Princess has dark green, thick, and wavy leaves that are held relatively upright giving the plant a pleasing rounded appearance as it becomes more mature.

I claim:

1. A new and distinct cultivar of Spathiphyllum plant named Princess, as illustrated and described.

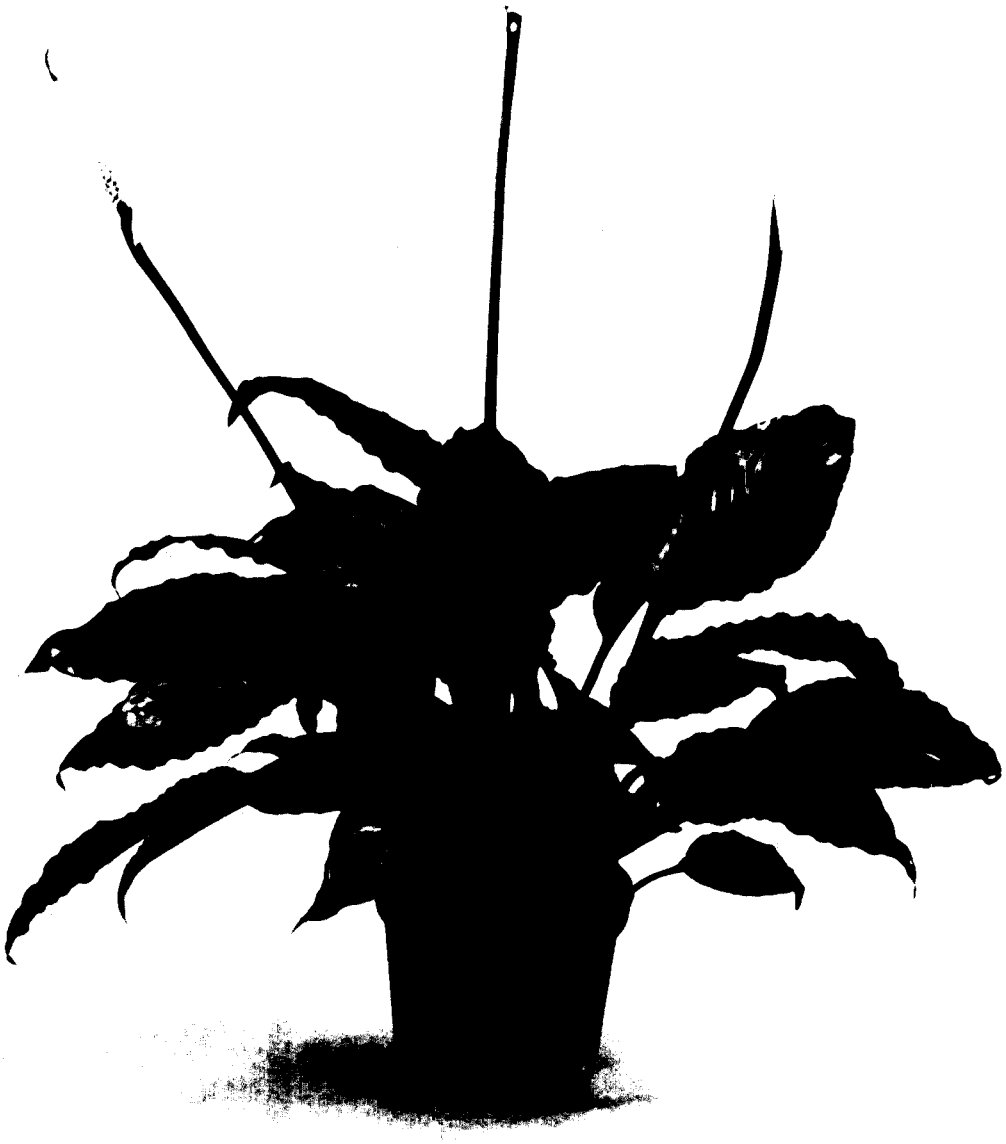

* * * * *